United States Patent
Kim et al.

(10) Patent No.: US 12,031,235 B2
(45) Date of Patent: Jul. 9, 2024

(54) NANOFIBER COMPOSITE MEMBRANE FOR GUIDED BONE REGENERATION, AND MANUFACTURING METHOD THEREFOR

(71) Applicant: AMOGREENTECH CO., LTD., Gimpo-si (KR)

(72) Inventors: Chan Kim, Gwangju (KR); Seung Hoon Lee, Paju-si (KR); Seon Ho Jang, Seoul (KR); Ji Hyun Lee, Incheon (KR); Yun Mi So, Incheon (KR)

(73) Assignee: AMOGREENTECH CO., LTD., Gimpo-si (KR)

( * ) Notice: Subject to any disclaimer, the term of this patent is extended or adjusted under 35 U.S.C. 154(b) by 845 days.

(21) Appl. No.: 17/151,308

(22) Filed: Jan. 18, 2021

(65) Prior Publication Data

US 2021/0140070 A1    May 13, 2021

Related U.S. Application Data

(63) Continuation-in-part of application No. 16/093,368, filed as application No. PCT/KR2017/004044 on Apr. 14, 2017, now abandoned.

(30) Foreign Application Priority Data

Apr. 28, 2016   (KR) .......................... 10-2016-0052342

(51) Int. Cl.
*A61L 27/54*   (2006.01)
*A61F 2/07*   (2013.01)
(Continued)

(52) U.S. Cl.
CPC .......... *D01D 5/003* (2013.01); *A61L 24/0042* (2013.01); *A61L 27/12* (2013.01);
(Continued)

(58) Field of Classification Search
None
See application file for complete search history.

(56) References Cited

U.S. PATENT DOCUMENTS 7,811,666 B2 * 10/2010 Dry ......................... C04B 28/02
                                                                   428/358
8,334,121 B2 * 12/2012 Schindler ............. C12N 5/0068
                                                                   435/320.1
(Continued)

FOREIGN PATENT DOCUMENTS

JP           61075817          4/1986
KR          100946268          3/2010
(Continued)

OTHER PUBLICATIONS

International Search Report—PCT/KR2017/004044 dated Jul. 19, 2017.

*Primary Examiner* — Ann Schillinger
(74) *Attorney, Agent, or Firm* — CANTOR COLBURN LLP

(57) ABSTRACT

Provided is a nanofiber composite membrane for guided bone regeneration, which includes: spinning a spinning solution by an electrospinning method to produce nanofibers; accumulating the nanofibers, to prepare a certain thickness of a nanofiber web; and drying and thermally calendering the nanofiber web to sterilize the nanofiber web, wherein the spinning solution contains a biocompatible plasticizer to maintain physical properties, flexibility and elasticity of the membrane, by suppressing an increase in brittleness in a sterilization treatment.

7 Claims, 6 Drawing Sheets

(51) Int. Cl.
- *A61L 24/00* (2006.01)
- *A61L 27/12* (2006.01)
- *A61L 27/26* (2006.01)
- *A61L 31/16* (2006.01)
- *D01D 5/00* (2006.01)
- *D01F 1/10* (2006.01)
- *B82Y 5/00* (2011.01)
- *B82Y 30/00* (2011.01)
- *B82Y 40/00* (2011.01)

(52) U.S. Cl.
CPC ......... *A61L 27/26* (2013.01); *A61L 2300/112* (2013.01); *A61L 2300/20* (2013.01); *A61L 2300/412* (2013.01); *A61L 2430/02* (2013.01); *A61L 2430/38* (2013.01); *B82Y 5/00* (2013.01); *B82Y 30/00* (2013.01); *B82Y 40/00* (2013.01)

(56) References Cited

U.S. PATENT DOCUMENTS

| | | | |
|---|---|---|---|
| 9,487,893 B2 * | 11/2016 | Moore | D01F 6/92 |
| 9,522,963 B2 * | 12/2016 | Tramontano | C08J 3/091 |
| 10,413,566 B2 * | 9/2019 | Ohri | A61K 33/24 |
| 10,561,766 B2 * | 2/2020 | Antoni | A61L 29/08 |
| 10,736,985 B2 * | 8/2020 | Odermatt | A61L 15/325 |
| 11,781,032 B2 * | 10/2023 | Catchmark | D21H 19/50 |
| | | | 106/162.2 |
| 11,839,698 B2 * | 12/2023 | Drumheller | A61L 31/10 |
| 2006/0095137 A1 * | 5/2006 | Chung | A61L 31/005 |
| | | | 264/28 |
| 2007/0098953 A1 * | 5/2007 | Stabelfeldt | A61F 13/60 |
| | | | 428/100 |
| 2011/0195123 A1 | 8/2011 | Shemi | |
| 2011/0236974 A1 | 9/2011 | Ogle et al. | |

FOREIGN PATENT DOCUMENTS

| | | |
|---|---|---|
| KR | 20120005878 | 1/2012 |
| KR | 101269127 | 5/2013 |
| KR | 101479206 | 1/2015 |
| KR | 20150082757 | 7/2015 |
| KR | 20160031683 | 3/2016 |

* cited by examiner

NANOFIBER COMPOSITE MEMBRANE FOR GUIDED BONE REGENERATION, AND MANUFACTURING METHOD THEREFOR

TECHNICAL FIELD

The present disclosure relates to a nanofiber composite membrane for guided bone regeneration comprising a nanofiber layer produced by an electrospinning method and a method of manufacturing the same.

BACKGROUND ART

With introduction to an aging society, in order to improve healing by introducing membranes (i.e., shielding membranes) in injured periodontal tissues to treat damaged alveolar bone due to a sudden increase in patients with bone disease, especially periodontal disease, and to induce restoration of periodontal tissue, guided bone regeneration (i.e., implant) is performed in various ways.

The membrane used for the guided bone regeneration is one of the implantable biomaterials used for inducing tissue and bone regeneration, and is used to form a space through the membrane, to provide a sufficient time for the migrated cells to proliferate, and at the same time, to block the migrated cells from moving to the other place and the penetration of epithelial cells.

These membranes are required to block fibroblasts originally having a size of about 5 μm to 15 μm and to have a pore structure through which blood, body fluids, and oxygen can pass smoothly, and serve as a role of sealing between bones thereby preventing fibrous connective tissues from being exposed to the defect site, preventing intrusion of adjacent fibrous connective tissues, stabilizing healing of wounds by preventing invasion of bacteria even if the fibrous connective tissues are exposed, and securing space suitable for functional reconstruction for bone regeneration.

The membranes are largely classified into absorbent and non-absorbent membranes. The absorbent membrane is mainly composed of biodegradable materials such as collagen type I and III, polylactic acid (PLA), polyglatin, polylactic-coglycolic acid (PLGA), or polyglycolic acid (PGA) and is decomposed after performing a barrier function for a certain period of time, and is classified into a cross-linked type and non-cross-linked type. The absorbent membrane is absorbed from at least 2 weeks up to 54 weeks, and does not require a further removal surgery.

These absorbent products act as a barrier even when the membrane is exposed to the outside or damaged, so that the risk of infection is low, and are used to block the mechanical stress applied to the wound.

As the material of the non-absorbent membrane, expanded polytetrafluoroethylene (e-PTFE), ethyl cellulose (EC), high density polytetrafluoroethylene (PTFE), freeze-dried dura mater (FDDMA), titanium (Ti), mesh, and so on are used.

The shielding membrane formed of such a non-absorbent material has excellent handling properties and space retaining ability. However, after sufficient bone restoration is performed, it is required to be removed by a secondary operation. Therefore, there is a possibility of causing an inflammatory reaction during the bone restoration period, and there is a drawback in that the patient burden is large due to the secondary operation.

Particularly, in the case of the absorbent membrane, it is known that osteoblast adhesion and affinity are insufficient compared to the non-absorbent material, and the bone regeneration is delayed somewhat. However, the side effect of the absorbent membrane is less than that of the non-absorbent membrane and most of the absorbent membranes receive the excellent evaluation even in safety.

However, when the absorbent membrane is used alone, the space securing ability of the absorbent membrane is somewhat lower than that of the non-absorbent membrane. To solve this problem, a method of ensuring a space by mixing and implanting the autologous bone or other bone substitute in a direction below the shielding membrane is applied. However, if membrane removal is necessary, it may be difficult to remove the membrane if the membrane is already absorbed to some degree. In addition, there is a possibility that the cells or bone may be degraded before sufficient proliferation, and there is a disadvantage of being absorbed into the new tissue by macrophage action and local inflammatory reaction.

Therefore, the absorbent membrane material and the non-absorbent membrane material should be appropriately used depending on the patient's condition.

Electrospinning technology, which has recently become a research and development boom, has been actively applied as a dental shielding membrane material because a porous membrane can be produced by accumulating nanofibers having a fiber diameter of less than 1 μm in a three-dimensional nonwoven fabric type.

Korean Patent Application Publication No. 10-2015-0082757 (Patent Document 1) discloses a polytetrafluoroethylene nanofiber membrane for guided bone regeneration and a method of manufacturing the same.

Patent Document 1 discloses a method of applying a nanofiber membrane as a membrane for guided bone regeneration, in which a polytetrafluoroethylene (PTFE) solution is mixed with a polyethylene oxide (PEO) solution, the mixture is electrospun and then heat-treated to remove the PEO component to thereby prepare a nanofiber composed of non-absorbent PTFE.

In the case of Patent Document 1, the PEO/PTFE composite nanofibers are heat-treated at a temperature of 200° C. to 400° C. to remove the PEO component to produce a nanofiber composed of PTFE. It is necessary to perform repetitive acid treatment or water washing treatment, in order to completely remove the residual PEO component after the heat-treatment, that is, ash, etc., and there is a problem that an inflammatory reaction or the like caused by residues should be solved. In addition, there are problems such as an increase in the process cost due to the heat-treatment and an increase in the brittleness due to the sterilization treatment of the PTFE nanofibers.

Korean Registered Patent Publication No. 10-0946268 (Patent Document 2) discloses a guided bone regeneration membrane and a method of producing the same. Patent Document 2 discloses a guided bone regeneration membrane including an outer layer structure of a porous semipermeable membrane type including a biodegradable polymer for medical use, and an amphiphilic polymer having a hydrophilic group and a hydrophobic group, and an inner layer structure having a fiber radial type mesh shape formed of a mixture of a biodegradable polymer for medical use and calcium phosphate.

Patent Document 2 discloses a method of manufacturing a double-structure absorbent membrane by forming a porous mesh layer and introducing a calcium phosphate-containing nanofiber layer.

The nanofiber composed of the biocompatible (bioabsorbable) polymer of Patent Document 2 has a disadvantage in that the brittleness is increased due to the breakage of the molecular chain constituting the nanofiber during the sterilization treatment such as ethylene oxide (EO) gas, steam, or gamma ray irradiation, and thus the physical properties are deteriorated. Accordingly, the nanofiber of Patent Document 2 has a problem in securing the space maintaining ability, due to the decomposition time faster than the decomposition time of the material, and has a concern of failing to bring the effect of a blocking membrane such as an inflammation reaction appropriately.

In addition, there is a fear that the process cost may increase due to the combination of different processes such as the formation of the porous mesh and the production of the nanofiber layer, and there is also a fear that the material itself may retain the hydrophobic property and move to other site without being correctly mounted on the treatment site.

DISCLOSURE

Technical Problem

Accordingly, an object of the present disclosure is to provide a nanofiber composite membrane for guided bone regeneration which can contain a biocompatible plasticizer and inhibit an increase in brittleness during sterilization treatment, thereby maintaining physical properties, flexibility and elasticity, and a method of manufacturing the nanofiber composite membrane.

Another object of the present disclosure is to provide a nanofiber composite membrane for guided bone regeneration comprising nanofiber layers of a multi-layered structure in which at least one nanofiber layer contains a guided bone material and a method of manufacturing the same.

Another object of the present disclosure is to provide a nanofiber composite membrane for guided bone regeneration of a double structure in which a non-absorbent nanofiber layer and an absorbent nanofiber layer are laminated and a method of manufacturing the same.

Technical Solution

In order to accomplish the above object, according to an aspect of the present disclosure, there is provided a nanofiber composite membrane for guided bone regeneration, which comprises: spinning a spinning solution by an electrospinning method to produce nanofibers; accumulating the nanofibers, to prepare a certain thickness of a nanofiber web; and drying and thermally calendering the nanofiber web to sterilize the nanofiber web, wherein the spinning solution contains a biocompatible plasticizer to maintain physical properties, flexibility and elasticity of the membrane.

The spinning solution may be prepared by mixing a non-absorbent polymer material, a biocompatible plasticizer and a solvent at a certain ratio.

The thickness of the membrane may be 0.15 mm to 0.5 mm.

As the non-absorbent polymer material, one selected from polyvinylidene difluoride (PVDF), polyacrylonitrile (PAN), polyethylenimine (PEI), and polyurethane (PU) or two or more copolymer derivatives may be used.

The mixing ratio of the non-absorbent polymer material may be 10% to 30% by weight.

The biocompatible plasticizer may comprise one or more selected from citrate group such as acetyl tributyl citrate (ATBC) and tributyl citrate (TBC), benzoate group such as glycerol tribenzoate and ethyl benzoate, glycerol, sorbitol, mannitol, propylene and glycol, or a combination thereof.

The mixing ratio of the biocompatible plasticizer may be 2% to 30% by weight relative to the non-absorbent polymer material.

The membrane may be sterilized by one or more selected from ethylene oxide (EO) gas treatment, steam treatment, and gamma irradiation, or a combination thereof.

According to another aspect of the present disclosure, a nanofiber composite membrane for guided bone regeneration may comprise: an outer layer which is formed by spinning a spinning solution which is obtained by mixing an electrospinnable absorbent polymer material, a biocompatible plasticizer and a solvent at a predetermined ratio by an electrospinning method to produce nanofibers and accumulating the nanofibers; and an inner layer which is laminated on the outer layer and which is formed by spinning a spinning solution which is obtained by mixing an electrospinnable absorbent polymer material, a biocompatible plasticizer, a guided bone regeneration material and a solvent at a predetermined ratio by an electrospinning method to produce nanofibers and accumulating the nanofibers.

The absorbent polymer material may employ one selected from a poly (lactic acid) group, a poly (glycolic acid) group, a poly (caprolactone) group and PLGA, or a combination of two or more copolymer derivatives.

The guided bone regeneration material may employ one selected from biodegradable calcium groups including hydroxyapatite (HA), β-tricalcium phosphate (β-TCP), and biphasic calcium phosphate (BCP), or a combination of two or more thereof.

According to another aspect of the present disclosure, a nanofiber composite membrane for guided bone regeneration may comprise: a non-absorbent membrane which is formed by spinning a spinning solution which is obtained by mixing an electrospinnable non-absorbent polymer material, a biocompatible plasticizer and a solvent at a predetermined ratio by an electrospinning method to produce nanofibers and accumulating the nanofibers; and an absorbent membrane which is laminated on the non-absorbent membrane and which is formed by spinning a spinning solution which is obtained by mixing an electrospinnable absorbent polymer material, a biocompatible plasticizer, a guided bone regeneration material and a solvent at a predetermined ratio by the electrospinning method to produce nanofibers and accumulating the nanofibers.

According to another aspect of the present disclosure, a method of manufacturing a nanofiber composite membrane for guided bone regeneration may comprise: preparing a spinning solution by mixing an electrospinning non-absorbent polymer material, a biocompatible plasticizer and a solvent at a predetermined ratio; spinning the spinning solution by an electrospinning method to produce nanofibers, and then accumulating the nanofiber to form a nanofiber membrane; drying and thermally calendering the nanofiber membrane in a certain thickness; and sterilizing the nanofiber membrane.

According to another aspect of the present disclosure, a method of manufacturing a nanofiber composite membrane for guided bone regeneration may comprise: preparing a first spinning solution in which an electrospinnable absorbent polymer material, a biocompatible plasticizer and a solvent are mixed at a predetermined ratio, and a second spinning solution in which an electrospinnable absorbent polymer material, a biocompatible plasticizer, a guided bone regeneration material and a solvent are mixed at a predetermined ratio; forming an outer layer by spinning the first spinning solution by an electrospinning method to produce nanofibers and accumulating the nanofibers; forming an inner layer by spinning the second spinning solution by the electrospinning method to produce nanofibers and accumulating the nanofibers; drying and thermal calendering a composite membrane which is formed by laminating the outer layer and the inner layer; and sterilizing the composite membrane.

According to another aspect of the present disclosure, a method of manufacturing a nanofiber composite membrane for guided bone regeneration may comprise: preparing a non-absorbent membrane which is formed by producing a spinning solution in which an electrospinnable non-absorbent polymer material, a biocompatible plasticizer, and a solvent are mixed at a predetermined ratio, and spinning the spinning solution by an electrospinning method to prepare nanofibers and to accumulate the nanofibers; preparing an absorbent membrane which is formed by producing a spinning solution in which an electrospinnable non-absorbent polymer material, a biocompatible plasticizer, a guided bone regeneration material and a solvent are mixed at a predetermined ratio, and spinning the spinning solution by an electrospinning method to prepare nanofibers and to accumulate the nanofibers; drying and thermal calendering a composite membrane which is formed in a certain thickness by laminating the non-absorbent membrane and the absorbent membrane; and sterilizing the composite membrane.

Advantageous Effects

As described above, the nanofiber composite membrane for guided bone regeneration according to an embodiment of the present disclosure contains a biocompatible plasticizer to suppress the increase of brittleness during the sterilization treatment, thereby maintaining flexibility and elasticity while maintaining physical properties.

In addition, it is possible to constitute nanofiber layers of a multi-layered structure, in which at least one nanofiber layer contains a guided bone material to improve the performance of the guided bone regeneration.

In addition, the non-absorbent nanofiber layer and the absorbent nanofiber layer may be formed of a laminated double structure to improve the performance of the guided bone regeneration by incorporating the guided bone material while having the advantages of the non-absorbent material.

BEST MODE

Figure 1:
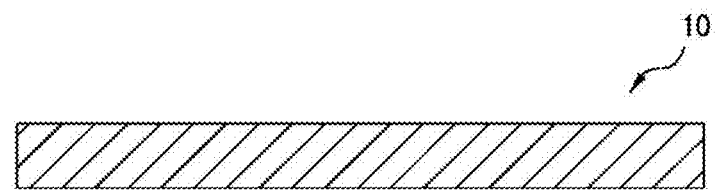
FIG. 1 is a cross-sectional view of a nanofiber composite membrane for guided bone regeneration according to a first embodiment of the present disclosure.

Hereinafter, embodiments of the present disclosure will be described in detail with reference to the accompanying drawings. The sizes and shapes of the components shown in the drawings may be exaggerated for clarity and convenience. In addition, terms defined in consideration of the configuration and operation of the present disclosure may vary depending on the intention or custom of the user, the operator, and the like. Definitions of these terms should be based on the content of this specification.

FIG. 1 is a cross-sectional view of a nanofiber composite membrane for guided bone regeneration according to a first embodiment of the present disclosure.

Referring to FIG. 1, a nanofiber composite membrane 10 according to a first embodiment of the present disclosure is prepared by mixing a non-absorbent polymer material and a solvent at a predetermined ratio to prepare a spinning solution having an electrospinnable concentration, electrospinning the spinning solution by an electrospinning method to produce nanofibers having a certain thickness, accumulating the nanofibers to a predetermined thickness to prepare a membrane, drying and thermal calendering the membrane, and sterilizing the membrane.

As the electrospinning method applied to the present disclosure, an upward type and a downward type each to which a nozzle is mounted, and a nozzleless type that can be spun without a nozzle may be used, and any one of an electrospray method, a centrifugal electrospinning method, a flash electrospinning method, a pulse electrospinning method, and a bubble electrospinning method may be used.

Here, the membrane is formed to have a thickness of 0.15 mm to 0.5 mm and is formed in a form having a plurality of pores so as to have a pore structure by which fibroblasts having a size of about 5 µM to 15 µM can be basically blocked, and through which blood, body fluids, oxygen, and the like can smoothly pass, and is also formed to seal between the bones, to prevent the fiber connective tissue from being exposed to the defect site, prevent intrusion of the adjacent fiber connective tissue, prevent the invasion of bacteria even if exposed, stabilize the wound healing, and secure a space suitable for functional reconstruction for bone regeneration.

As the applicable non-absorbent polymer material, one selected from polyvinylidene fluoride (PVDF), polyacrylonitrile (PAN), polyethyleneimide (PEI), and polyurethane (PU) or two or more copolymer derivatives may be used.

It is preferable that the non-absorbent polymer material is prepared so as to be 10% to 30% by weight based on the spinning solution.

The biocompatible plasticizer may comprise one selected from citrate group such as acetyl tributyl citrate (ATBC) and tributyl citrate (TBC), benzoate group such as glycerol tribenzoate and ethyl benzoate, glycerol, sorbitol, mannitol, propylene and glycol, or a combination of two or more thereof.

The biocompatible plasticizer is preferably used in an amount of 2% to 30% by weight, more preferably 2% to 20% by weight, based on the weight of the polymer.

The sterilization method may be one selected from the group consisting of EO gas treatment, steam treatment, and gamma irradiation, or a combination of two or more thereof.

As described above, the nanofiber composite membrane 10 according to the first embodiment may include a biocompatible plasticizer in addition to the non-absorbent polymer material, and may maintain physical properties, flexibility and elasticity without increasing the brittleness of the nanofibers during the sterilization treatment.

Figure 2:
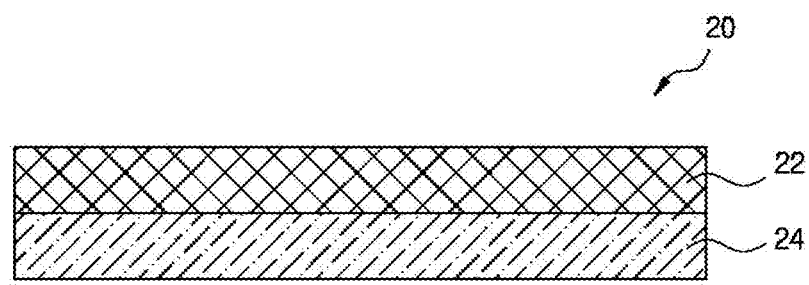
FIG. 2 is a cross-sectional view of a nanofiber composite membrane for guided bone regeneration according to a second embodiment of the present disclosure.

As shown in FIG. 2, a nanofiber composite membrane 20 for guided bone regeneration according to a second embodiment includes: an outer layer 22 formed by mixing an electrospinnable absorbent polymer material, a biocompatible plasticizer and a solvent in a certain ratio, to produce a spinning solution, spinning the spinning solution by an electrospinning method, to produce nanofibers, and accumulating the nanofibers; and an inner layer 24 laminated on the outer layer 22 and formed by mixing an electrospinnable absorbent polymer material, a biocompatible plasticizer, a guided bone regeneration material and a solvent in a certain ratio, to produce a spinning solution, spinning the spinning solution by the electrospinning method, to produce nanofibers, and accumulating the nanofibers.

The outer layer 22 and the inner layer 24 are dried and subjected to thermal calendering to have a thickness of 0.15 mm to 0.5 mm and sterilized.

Here, the outer layer 22 and the inner layer 24 may be integrally formed in one electrospinning device, or may be separately formed and then laminated on together.

As the biocompatible plasticizer, the same plasticizer as the biocompatible plasticizer described in the first embodiment can be used.

The absorbent polymer material may employ one selected from a poly (lactic acid) group, a poly (glycolic acid) group, a poly (caprolactone) group and PLGA, or two or more copolymer derivatives.

The guided bone regeneration material may employ one selected from biodegradable calcium groups including hydroxyapatite (HA), β-tricalcium phosphate (β-TCP), and biphasic calcium phosphate (BCP), or a combination of two or more thereof.

As described above, since the nanofiber composite membrane 20 according to the second embodiment is made of a biodegradable material using an absorbent polymer material, and is decomposed after performing a barrier function for a certain period of time, it is not necessary to remove the membrane.

In addition, the nanofiber composite membrane 20 according to the second embodiment may include a biocompatible plasticizer in addition to the absorbent polymer material, and may maintain physical properties, flexibility and elasticity without increasing the brittleness of the nanofibers during the sterilization treatment.

In addition, the nanofiber composite membrane 20 according to the second embodiment has the inner layer 24 containing the guided bone regeneration material in the absorbent polymer material, thereby performing bone regeneration while acting as a shielding membrane.

Figure 3:
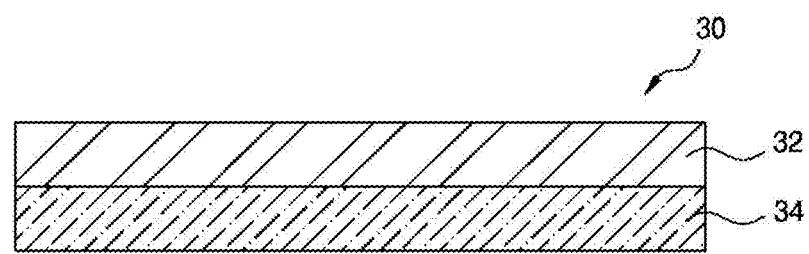
FIG. 3 is a cross-sectional view of a nanofiber composite membrane for guided bone regeneration according to a third embodiment of the present disclosure.

As shown in FIG. 3, a nanofiber composite membrane 30 for guided bone regeneration according to a third embodiment includes: a non-absorbent membrane 32 formed by mixing an electrospinnable non-absorbent polymer material, a biocompatible plasticizer and a solvent in a certain ratio, to produce a spinning solution, spinning the spinning solution by an electrospinning method, to produce nanofibers, and accumulating the nanofibers; and an absorbent membrane 34 laminated on the non-absorbent membrane 22 and formed by mixing an electrospinnable absorbent polymer material, a biocompatible plasticizer, a guided bone regeneration material and a solvent in a certain ratio, to produce a spinning solution, spinning the spinning solution by the electrospinning method, to produce nanofibers, and accumulating the nanofibers.

Then, the non-absorbent membrane 32 and the absorbent membrane 34 are dried and thermally calendered to have a thickness of 0.15 mm to 0.5 mm and sterilized.

Here, the non-absorbent membrane 32 and the absorbent membrane 34 may be sequentially formed in one electrospinning device, or may be separately formed and then laminated on together.

The non-absorbent membrane 32 is the same as the nanofiber composite membrane 10 described in the first embodiment and the absorbent membrane 34 is the same as the inner layer 24 described in the second embodiment.

The nanofiber composite membrane 30 according to the third embodiment is provided with the non-absorbent membrane 32 and the absorbent membrane 34 at the same time, and is excellent in handleability, which is an advantage of the non-absorbent membrane. In addition, the nanofiber composite membrane 30 may have a space-maintaining ability to achieve sufficient bone restoration and may include a guided bone regeneration material to accelerate bone regeneration.

The nanofiber composite membrane 30 according to the third embodiment includes a biocompatible plasticizer to maintain physical properties, flexibility and elasticity without increasing the brittleness of the nanofibers during the sterilization treatment.

Next, a method of manufacturing a nanofiber composite membrane will be described.

Figure 4:
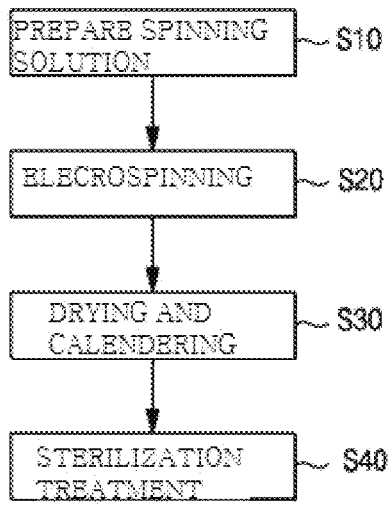
FIG. 4 is a flowchart illustrating a method of manufacturing a nanofiber composite membrane for guided bone regeneration according to the first embodiment of the present disclosure.

FIG. 4 is a flowchart illustrating a method of manufacturing a nanofiber composite membrane according to the first embodiment of the present disclosure.

First, the non-absorbent polymer material is dissolved in a solvent at an electrospinnable concentration and a biocompatible plasticizer is mixed therein to prepare a spinning solution (S10).

Here, the non-absorbent polymer material is preferably added in an amount of 10% to 30% by weight based on the spinning solution to prepare a spinning liquid. However, in the case that the concentration of the non-absorbent polymer material exceeds 30% by weight, the viscosity of the spinning solution may be too high to form nanofibers. Otherwise, in the case that the concentration of the non-absorbent polymer material is less than 10% by weight, a fiber shape may not be maintained and a bead shape may be formed, so that the final desired nanofiber membrane may not be produced.

The biocompatible plasticizer is preferably used in an amount of 2% to 30% by weight, more preferably 2% to 20% by weight, based on the polymer material. However, in the case that the amount of the biocompatible plasticizer exceeds 30% by weight, there is a possibility that the plasticization or the reaction may proceed excessively, or spin trouble such as bead formation may be caused during the nanofiber formation. In the case that the amount is less than 2% by weight, the plasticizing reaction becomes insufficient and the final nanofiber may be deteriorated in physical properties.

Thus, the spinning solution is transported to a spin pack, and at this time, a voltage is applied to the spin pack by using a high voltage device to conduct electrospinning. In this case, the voltage used can be adjusted from 0.5 KV to 100 KV, and the collector can be grounded or charged with negative (−) polarity. In the case of the collector, it is advisable to use a suction collector in order to smooth focusing of fibers during spinning.

It is also preferable to adjust the distance between the spin pack and the collector to a range of 5 cm to 50 cm. It is preferable that a discharge amount during spinning should be discharged and spun equally by using a metering pump, and the spinning is performed in an environment of a relative humidity of 30% to 80% in a chamber capable of controlling temperature and humidity during spinning.

In some embodiments of the present disclosure, a nanofiber web is formed by electrospinning the spinning solution from the spin pack on one side of a transfer sheet conveyed along a collector on the lower side of the spin pack using the electrospinning method to produce nanofibers and then accumulating the nanofibers (S20). The nanofiber web collected on the transfer sheet has nanofibers accumulated and has three-dimensional micropores.

The thus fabricated nanofiber web is dried and calendered to form a fixed pore structure that forms a bond between the nanofibers (S30). At this time, calendering is performed at a temperature of 100° C. to 200° C. under a condition of 0.5 Kgf/cd to 1.5 Kgf/cd.

Then, sterilization treatment is performed to produce a non-absorbent nanofiber composite membrane (S40).

Figure 5:
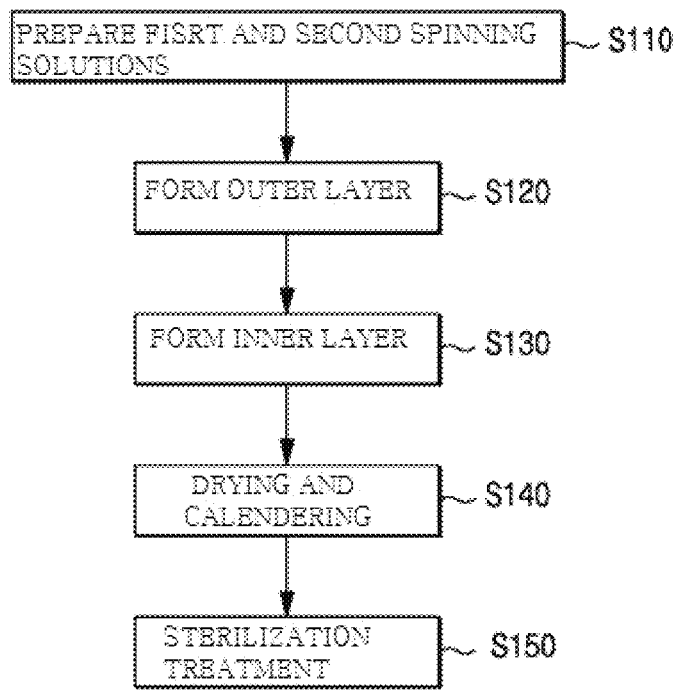
FIG. 5 is a flowchart illustrating a method of manufacturing a nanofiber composite membrane for guided bone regeneration according to the second embodiment of the present disclosure.

FIG. 5 is a flowchart illustrating a method of manufacturing a nanofiber composite membrane according to the second embodiment of the present disclosure.

First, an electrospinnable absorbent polymer material is dissolved in a solvent at an electrospinnable concentration, and then a biocompatible plasticizer is mixed therein to dissolve a first spinning solution and the electrospinnable absorbent polymer material in the solvent at an electrospinnable concentration. Then, a biocompatible plasticizer and a guided bone regeneration material are mixed therein to prepare a second spinning solution (S110).

Then, the first spinning solution is spun by an electrospinning method to produce nanofibers, and the nanofibers are accumulated to form an outer layer 22 (S120). The electrospinning method of the first spinning solution is the same as the electrospinning method described in the first embodiment.

Then, the second spinning solution is spun by the electrospinning method on the outer layer 22 to produce nanofibers, and the nanofibers are accumulated to form an inner layer 24 (S130). The electrospinning method of the second spinning solution is the same as the electrospinning method described in the first embodiment.

Here, the guided bone regeneration material is preferably added in an amount of 5% to 20% by weight relative to the absorbent polymer material. However, in the case that the content of the guided bone regeneration material exceeds 20% by weight, it is difficult to form nanofibers or the possibility of occurrence of spin trouble such as clogging of the nozzle increases. Otherwise, in the case that the content of the guided bone regeneration material is less than 5% by weight, there is a possibility that the effect of guiding bone regeneration may not be exhibited properly.

Then, a fixed pore structure is implemented by drying and calendering the composite membrane in which the outer layer 22 and the inner layer 24 are laminated to form a bond between the nanofibers (S140).

Then, sterilization treatment is performed to produce an absorbent nanofiber composite membrane (S150).

Figure 6:
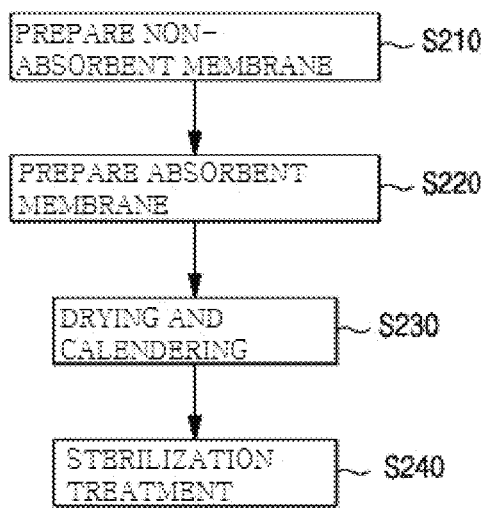
FIG. 6 is a flowchart illustrating a method of manufacturing a nanofiber composite membrane for guided bone regeneration according to the third embodiment of the present disclosure.

FIG. 6 is a flowchart illustrating a method of manufacturing a nanofiber composite membrane according to the third embodiment of the present disclosure.

First, a non-absorbent membrane 32 is formed by producing a spinning solution in which an electrospinnable non-absorbent polymer material, a biocompatible plasticizer, and a solvent are mixed at a predetermined ratio, and spinning the spinning solution by an electrospinning method to prepare nanofibers and accumulating the nanofibers (S210).

Here, the non-absorbent membrane 32 can be manufactured by the same manufacturing process as the non-absorbent nanofiber composite membrane described in the first embodiment.

Then, a spinning solution is prepared by mixing an electrospinnable absorbent polymer material, a biocompatible plasticizer, a guided bone regeneration material and a solvent at a predetermined ratio, the spinning solution is spun on a non-absorbent membrane by an electrospinning method to produce nanofibers, and the nanofibers are accumulated to produce an absorbent membrane 34 (S220).

Here, the absorbent membrane 34 can be manufactured by the same manufacturing process as the inner layer described in the second embodiment.

A composite membrane in which a non-absorbent membrane 30 and an absorbent membrane 34 are laminated is dried and calendered to implement a fixed pore structure to form a bond between nanofibers (S230).

Then, the composite membrane is sterilized to produce a non-absorbent and absorbent nanofiber composite membrane (S240).

Example 1

PVDF as a fiber-forming polymer was dissolved in a mixed solution such as DMAc/acetone to become 15% by weight based on the spinning solution, and sorbitol was added as a plasticizer to become 5% by weight of PVDF to prepare a composite spinning solution.

Figure 7A:
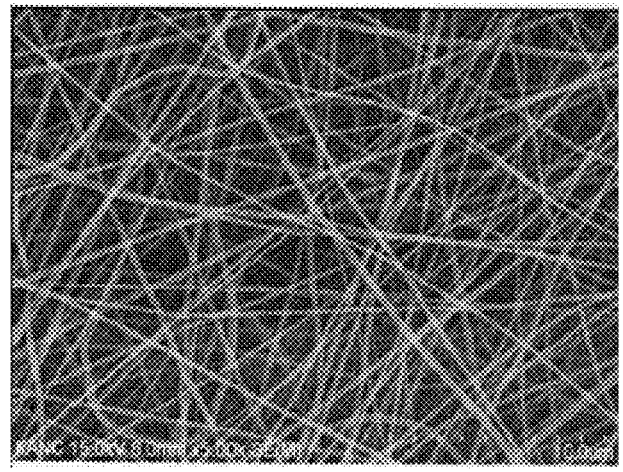
FIGS. 7A and 7B are Scanning Electron Microscope (SEM) micrographs of the surface of the electrospun nanofiber layer according to the first embodiment of the present disclosure.
Figure 7B:
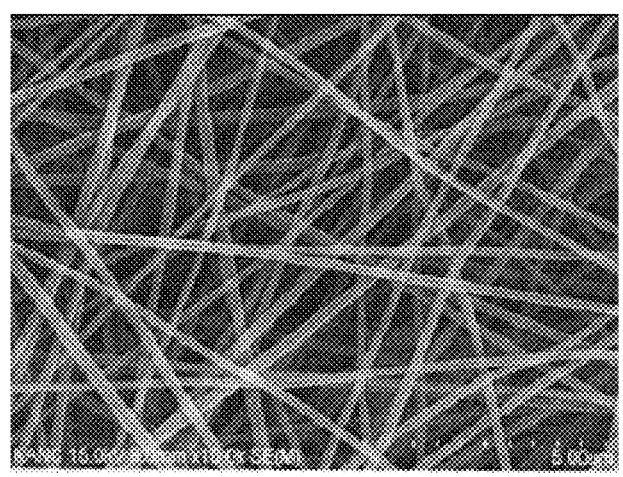

The prepared spinning solution was subjected to be electrospun by using an electrospinning device under the conditions of an applied voltage of 25 KV, a distance of 25 cm from a collector to a spin hole, and a discharge amount of 0.05 ml/hole in an environment of relative humidity (RH) of 65% and a temperature of 30° C., nanofibers with a smooth nanofiber surface and an average diameter of about 230 nm were obtained as shown in FIGS. 7A and 7B.

Figure 8A:
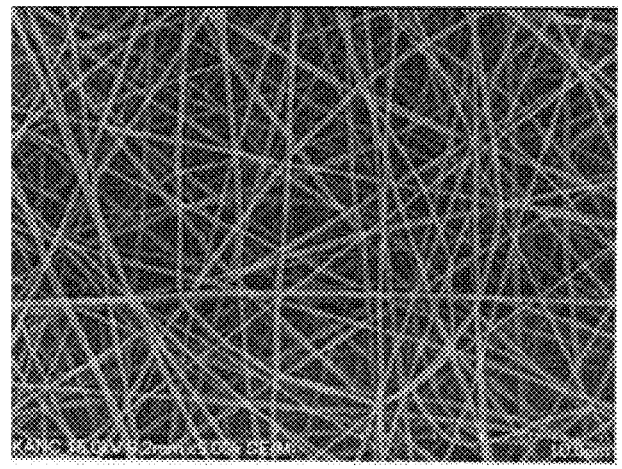
FIGS. 8A and 8B are SEM micrographs of the surface of the sterilized nanofiber layer according to the first embodiment of the present disclosure.
Figure 8B:
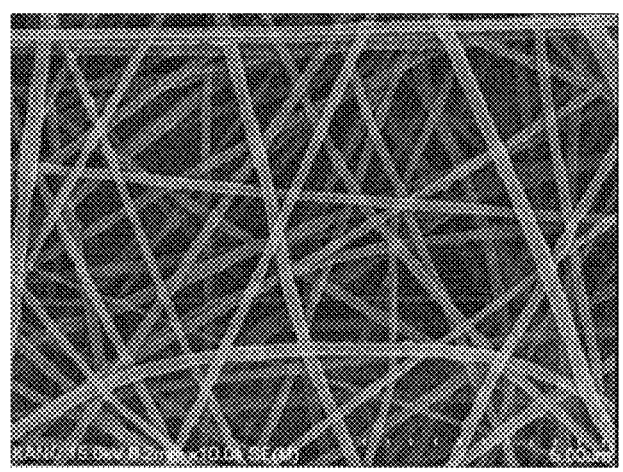

The nanofibers prepared as described above were sterilized by irradiating γ-ray (gamma ray) of G company. In this case, the irradiation amount was set to 25 KGT. As a result of the surface morphology analysis of the sterilized samples, it was found that there was no change in the surface structure of the fibers, as shown in FIGS. 8A and 8B, when compared with the samples before the sterilization treatment as shown in FIGS. 7A and 7B.

Example 2

PLGA as an absorbent polymer was dissolved in a mixed solution such as DMAc/acetone to become 15% by weight based on the spinning solution, and sorbitol was added as a plasticizer to become 5% by weight of PLGA to prepare a first composite spinning solution. After preparing a solution having the same composition as the composite spinning solution, 10% by weight of tricalcium phosphate (TCP) was added to the PLGA polymer to prepare a second composite spinning solution.

The first composite spinning solution prepared above was electrospun under the same conditions as in Example 1 by using an electrospinning device, to prepare PLGA nanofibers, and then the second composite spinning solution was electrospun on the prepared PLGA nanofibers in the same manner as the electrospinning conditions of Example 1 to form two-layer PLGA nanofibers.

The prepared two-layer PLGA nanofibers were squeezed through a calender roll, and sterilized in the same manner as in Example 1.

Figure 9A:
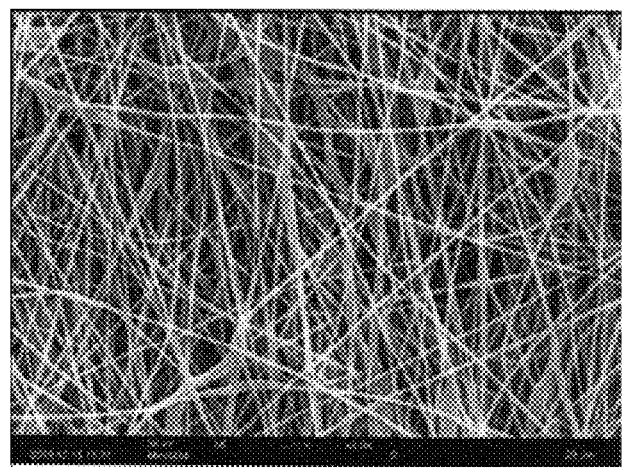
FIG. 9A is a SEM photograph of the surface of a nanofiber layer prepared by electrospinning a first composite solution according to the second embodiment of the present disclosure.
Figure 9B:
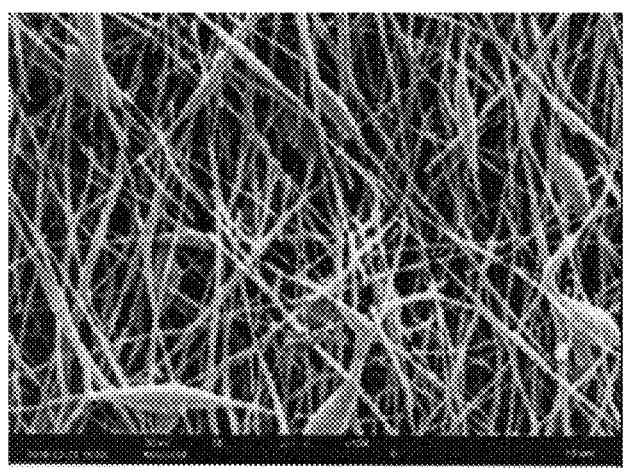
FIG. 9B is a SEM photograph of the surface of a nanofiber layer prepared by electrospinning a second composite solution according to the second embodiment of the present disclosure.

As shown in FIGS. 9A and 9B, an outer PLGA layer and an inner TCP-containing PLGA layer were observed through a scanning electron microscope for the morphology analysis of the surfaces of the nanofibers. FIG. 9A shows that a bead shape is observed in the nanofiber on the surface of the PLGA containing no TCP. In the case of the PLGA containing TCP as shown in FIG. 9B, it can be seen that the bead shape is more distributed and the length of the fiber is shorter in comparison with FIG. 9A. This phenomenon is a result of reduction of spinnability during electrospinning by the containing of TCP.

Example 3

A non-absorbent/absorbent nanofiber composite membrane was prepared by electrospinning the second composite spinning solution of Example 2 to the nanofiber layer prepared by the method of Example 1 in the same manner as the electrospinning conditions of Example 1. The prepared nanofiber composite membrane was subjected to calendering heated to 130° C. to prepare a two-layer asymmetric composite membrane.

The prepared membrane was subjected to sterilization treatment under the same conditions as in the method of Example 1. As a result of the sterilization treatment, it was confirmed that an asymmetric composite membrane having both flexibility and elasticity was produced without damaging the fibers.

While the present disclosure has been particularly shown and described with reference to exemplary embodiments thereof, by way of illustration and example only, it is clearly understood that the present disclosure is not to be construed as limiting the present disclosure, and various changes and modifications may be made by those skilled in the art within the protective scope of the invention without departing off the spirit of the present disclosure.

INDUSTRIAL APPLICABILITY

The present disclosure relates to a nanofiber composite membrane for guided bone regeneration which can contain a biocompatible plasticizer and can suppress an increase in brittleness during sterilization treatment and maintain physical properties, flexibility and elasticity, and a method of manufacturing the composite membrane, and can be applied to guided bone regeneration (implant) that guides restoration of periodontal tissues.

What is claimed is:

1. A method of manufacturing a nanofiber composite membrane for guided bone regeneration, the method comprising:
    preparing a first spinning solution by mixing an electro-spinnable non-absorbent polymer material, a biocompatible plasticizer, and a solvent at a predetermined ratio;
    electro-spinning the first spinning solution to form a non-absorbent membrane made of first accumulated electro-spun nanofibers;
    prepare a second spinning solution by mixing an electro-spinnable non-absorbent polymer material, a biocompatible plasticizer, a guided bone regeneration material and a solvent at a predetermined ratio;
    electro-spinning the second spinning solution to form an absorbent membrane made of second accumulated electro-spun nanofibers;
    laminating the non-absorbent membrane and the absorbent membrane to form a composite membrane; and
    thermal calendaring the composite membrane having a certain thickness.

2. The method of claim 1, wherein the electro-spinnable non-absorbent polymer material includes: one selected from the group consisting of a poly (lactic acid) group, a poly (glycolic acid) group, a poly (caprolactone) group, PLGA, and a combination of two or more copolymer derivatives thereof.

3. The method of claim 1, wherein the guided bone regeneration material employs one selected from the group consisting of hydroxyapatite (HA), β-tricalcium phosphate (β-TCP), biphasic calcium phosphate (BCP), and a combination of two or more thereof.

4. The method of claim 1, wherein the certain thickness is in a range of 0.15 mm to 0.5 mm.

5. The method of claim 1, wherein a mixing ratio of the non-absorbent polymer material is in a range of 10% to 30% by weight.

6. The method of claim 1, wherein a mixing ratio of the biocompatible plasticizer is in a range of 2% to 30% by weight relative to the non-absorbent polymer material.

7. The method of claim 1, further comprising: sterilizing the composite membrane using one or more selected from the group consisting of EO gas treatment, steam treatment, and gamma irradiation, and a combination thereof.

* * * * *